United States Patent
Suchanek et al.

(10) Patent No.: US 10,040,773 B2
(45) Date of Patent: Aug. 7, 2018

(54) SILVER CATALYSTS WITH IMPROVED SIZE AND DISTRIBUTION DENSITY OF SILVER PARTICLES

(71) Applicant: Scientific Design Company, Inc., Little Ferry, NJ (US)

(72) Inventors: Wojciech L. Suchanek, Wyckoff, NJ (US); Nabil Rizkalla, River Vale, NJ (US); Andrzej Rokicki, Mountain Lakes, NJ (US)

(73) Assignee: Scientific Design Company, Inc., Little Ferry, NJ (US)

( * ) Notice: Subject to any disclaimer, the term of this patent is extended or adjusted under 35 U.S.C. 154(b) by 0 days.

(21) Appl. No.: 15/054,447

(22) Filed: Feb. 26, 2016

(65) Prior Publication Data

US 2016/0251326 A1    Sep. 1, 2016

Related U.S. Application Data

(60) Provisional application No. 62/121,675, filed on Feb. 27, 2015.

(51) Int. Cl.
| | |
|---|---|
| *B01J 23/50* | (2006.01) |
| *C07D 301/10* | (2006.01) |
| *B01J 23/68* | (2006.01) |
| *B01J 35/10* | (2006.01) |
| *B01J 21/04* | (2006.01) |
| *B01J 35/00* | (2006.01) |
| *B01J 35/02* | (2006.01) |

(52) U.S. Cl.
CPC ............ *C07D 301/10* (2013.01); *B01J 21/04* (2013.01); *B01J 23/688* (2013.01); *B01J 35/006* (2013.01); *B01J 35/0013* (2013.01); *B01J 35/0066* (2013.01); *B01J 35/1009* (2013.01); *B01J 35/1038* (2013.01); *B01J 35/1042* (2013.01); *B01J 35/1061* (2013.01); *B01J 35/1066* (2013.01); *B01J 35/1071* (2013.01); *B01J 35/1076* (2013.01); *B01J 35/023* (2013.01)

(58) Field of Classification Search
CPC ... C07D 301/10; B01J 23/688; B01J 35/1076; B01J 35/1071; B01J 35/1066; B01J 35/1061; B01J 35/1042; B01J 35/1038; B01J 35/1009; B01J 35/023
USPC .......................................... 549/534; 502/347
See application file for complete search history.

(56) References Cited

U.S. PATENT DOCUMENTS

| | | | |
|---|---|---|---|
| 3,563,914 | A | 2/1971 | Wattimena |
| 3,702,259 | A | 11/1972 | Nielsen |
| 4,207,210 | A | 6/1980 | Kilty |
| 4,226,782 | A | 10/1980 | Hayden et al. |
| 4,242,235 | A | 12/1980 | Cognion et al. |
| 4,690,913 | A | 9/1987 | Nojiri et al. |
| 4,761,394 | A | 8/1988 | Lauritzen |
| 4,766,105 | A | 8/1988 | Lauritzen |
| 4,786,624 | A | 11/1988 | Nojiri et al. |
| 4,908,343 | A | 3/1990 | Bhasin |
| 4,994,589 | A | 2/1991 | Notermann |
| 5,011,807 | A | 8/1991 | Hayden et al. |
| 5,057,481 | A | 10/1991 | Bhasin |
| 5,099,041 | A | 3/1992 | Hayden et al. |
| 5,102,848 | A | 4/1992 | Soo et al. |
| 5,187,140 | A | 2/1993 | Thorsteinson et al. |
| 5,266,548 | A | 11/1993 | Koradia et al. |
| 5,380,697 | A | 1/1995 | Matusz et al. |
| 5,407,888 | A | 4/1995 | Herzog et al. |
| 5,502,020 | A | 3/1996 | Iwakura et al. |
| 5,525,740 | A * | 6/1996 | Rizkalla ............. B01J 23/50 502/347 |
| 5,597,773 | A | 1/1997 | Evans et al. |
| 5,691,269 | A | 11/1997 | Rizkalla |
| 5,831,037 | A | 11/1998 | Ohsuga et al. |
| 6,831,037 | B2 | 12/2004 | Szymanski et al. |
| 2004/0110973 | A1 | 6/2004 | Matusz |
| 2005/0096219 | A1 | 5/2005 | Szymanski et al. |
| 2012/0323026 | A1 | 12/2012 | Lockemeyer et al. |

FOREIGN PATENT DOCUMENTS

| | | |
|---|---|---|
| EP | 0624398 A1 | 11/1994 |
| WO | 94/02244 A1 | 2/1994 |

OTHER PUBLICATIONS

Sakai, Y., et al., "A novel silver catalyst prepared by using superheated-steam as a heating medium for ethylene oxide production", Catalysis Surveys from Asia, Sep. 1997, pp. 247-256, vol. 1, Issue 2.

International Search Report dated May 19, 2016 received in a corresponding foreign application.

* cited by examiner

*Primary Examiner* — Taylor V Oh

(74) *Attorney, Agent, or Firm* — Scully Scott Murphy and Presser

(57) ABSTRACT

A silver-based ethylene epoxidation catalyst is provided that exhibits improved performance, i.e., selectivity and activity decline. The catalyst that exhibits the improved performance includes greater than about 20% by weight of silver disposed on an alpha-alumina carrier, and a promoting amount of one or more promoters disposed on the alpha-alumina carrier. The silver is present on the alpha-alumina carrier as silver particles having a diameter of greater than about 150 nm and a distribution density of about 20 particles per 1 square micron or less.

15 Claims, No Drawings

SILVER CATALYSTS WITH IMPROVED
SIZE AND DISTRIBUTION DENSITY OF
SILVER PARTICLES

CROSS REFERENCE TO RELATED APPLICATION

The present invention claims the benefit of U.S. Provisional Patent Application No. 62/121,675 filed Feb. 27, 2015, the entire content and disclosure of which is incorporated herein by reference.

FIELD OF THE INVENTION

The present invention relates to ethylene epoxidation catalysts, and more particularly, to silver-based ethylene epoxidation catalysts having an improved useful lifetime.

BACKGROUND

As known in the art, high selectivity catalysts (HSCs) for the epoxidation of ethylene refer to those catalysts that possess selectivity values higher than high activity catalysts (HACs) used for the same purpose. Both types of catalysts include silver as the active catalytic component on a refractory support (i.e., carrier). Typically, one or more promoters are included in the catalyst to improve or adjust properties of the catalyst, such as selectivity.

Generally, but not necessarily always, HSCs achieve the higher selectivity (typically, in excess of 87 mole % or above) by incorporation of rhenium as a promoter. Typically, one or more additional promoters selected from alkali metals (e.g., cesium, potassium, lithium), and their mixtures, transition metals, and main group metals can also be included. In some cases HSCs did not include rhenium, yet achieve the high selectivity mentioned above.

There are also ethylene epoxidation catalysts that may not possess the selectivity values typically associated with HSCs, though the selectivity values are improved over HACs. These types of catalysts can also be considered within the class of HSCs, or alternatively, they can be considered to belong to a separate class, e.g., "medium selectivity catalysts" or "MSCs." These types of catalysts typically exhibit selectivities of at least 83 mole % and up to 87 mole %.

It is well known that with extended use of a catalyst, the catalyst will age (i.e., degrade) to a point until use of the catalyst is no longer practical. There is thus a continuous effort to extend the useful lifetime (i.e., "longevity" or "usable life") of catalysts. The useful lifetime of the catalyst is directly dependent on the stability of the catalyst. As used herein, the "useful lifetime" is the time period for which a catalyst can be used until one or more of its functional parameters, such as selectivity or activity, degrade to such a level that use of the catalyst becomes impractical.

Stability of the catalyst has largely been attributed to various characteristics of the carrier. Some characteristics of the carrier that have undergone much research include carrier formulation, surface area, porosity, and pore volume distribution, among others.

The most widely used formulation for the carriers of ethylene epoxidation catalysts are those based on alumina, typically alpha-alumina. Much research has been directed to investigating the effect of the alumina composition for improving stability and other properties of the catalyst. The preparation and modification of alumina carriers for enhancing ethylene epoxidation catalyst performance are described, for example, in U.S. Pat. Nos. 4,226,782, 4,242,235, 5,266,548, 5,380,697, 5,597,773, 5,831,037 and 6,831,037 as well as in U.S. Patent Application Publication Nos. 2004/0110973 A1 and 2005/0096219 A1.

Despite the above, there remains a need in the art for further improvements in the useful lifetime of ethylene epoxidation catalysts. There is a particular need for improving the stability of such catalysts by means that are facile and financially feasible.

SUMMARY

In one aspect of the present invention, a silver-based ethylene epoxidation catalyst having improved useful lifetime (as observed by having a reduced selectivity decline rate and/or a reduced activity decline rate) is provided. In one embodiment of the present invention, the silver-based ethylene epoxidation catalyst of the present invention includes greater than about 20% by weight of silver disposed on an alpha-alumina carrier, and a promoting amount of one or more promoters disposed on the alpha-alumina carrier. In accordance with the present invention, the silver is present on the alpha-alumina carrier as silver particles having a diameter of greater than about 150 nm and a distribution density of about 20 particles per 1 square micron or less.

In another aspect of the present invention, a process for the vapor phase conversion of ethylene to ethylene oxide in the presence of oxygen is provided. The method of the present invention includes providing the silver-based ethylene epoxidation catalyst of the present invention to an ethylene oxide reactor, and reacting a reaction mixture comprising ethylene and oxygen in the presence of the ethylene epoxidation catalyst of the present invention.

DETAILED DESCRIPTION

The problem of selectivity and activity decline of silver-based catalysts overtime has been typically associated with the coalescence and growth of silver particles during catalyst use, which is caused by the motion of the silver particles on the carrier surface. While in use, the silver particles gradually become larger (diameter increase) and simultaneously their distribution density decreases (i.e., there is less silver particles per surface area of the carrier), which ultimately results in loss of activity and selectivity decline.

As a result of the foregoing, a silver-based ethylene epoxidation catalyst is provided that exhibits improved selectivity and activity decline rates. The term "improved selectivity decline rate" is used throughout the present application to denote a catalyst selectivity decrease during a defined period of time ($\Delta S/\Delta t$), which is less than $\Delta S/\Delta t$ of the reference (i.e. not improved) catalyst; $\Delta S$ denotes a change in selectivity, while $\Delta t$ denotes a change in time. The term "improved activity decline rate" is used throughout the present application to denote a catalyst temperature increase during a defined period of time ($\Delta T/\Delta t$), which is less than $\Delta T/\Delta t$ of the reference (i.e. not improved) catalyst; $\Delta T$ is a change in temperature, while $\Delta t$ is a change in time. Throughout the present application, various elements from the Periodic Table of Elements are defined utilizing the IUPAC nomenclature. The silver particle size disclosed herein is an average silver particle size. By "average silver particle size" it is meant an average Ag particle diameter, as measured from SEM pictures taken either on as-synthesized catalysts, or on used catalysts, i.e., after completion of laboratory micro-reactors testing (at least 200 particles are measured altogether in 8 randomly selected areas of the catalyst).

In the present invention, the problem of selectivity and activity decline of a silver-based ethylene epoxidation catalyst overtime has been solved by controlled modification of size and distribution density of silver particles on an alpha-alumina carrier. Notably, it has been determined that when greater than about 20% by weight of silver is deposited on an alpha-alumina carrier and when the silver is present on the alpha-alumina carrier as silver particles having a diameter of greater than about 150 nm and a distribution density of about 20 particles per 1 square micron or less, a catalyst is provided that has improved useful lifetime as evident by having a reduced selectivity decline rate and/or a reduced activity decline rate as compared to a catalyst that does not include the high amount of silver, the silver particle size and silver particle distribution density. As used throughout the present invention, the term "about" generally indicates no more than ±10%, ±5%, ±2%, ±1% or ±0.5% from a number.

The carrier that can be employed in the present invention is an alpha-alumina carrier that can be prepared utilizing procedures well known in the art. In one embodiment and for example, an alumina carrier can be made by mixing a high-purity (greater than about 80%) alpha-alumina with temporary and permanent binders. The temporary binders, that include burnout materials, are thermally decomposable organic compounds of moderate to high molecular weight which, on decomposition, enhance the pore structure of the carrier. The temporary binders are essentially removed during firing when producing the final carrier. Some examples of burnout materials include cellulose, substituted celluloses, e.g., methylcellulose, ethylcellulose, and carboxyethylcellulose, stearates (e.g., organic stearate esters, such as methyl or ethyl stearate), waxes, granulated polyolefins (e.g., polyethylene and polypropylene), walnut shell flour, and the like, which are decomposable at the firing temperatures used in preparation of an alumina carrier.

The permanent binders are typically inorganic clay-type materials having fusion temperatures below that of the alumina, such as silica, aluminum, calcium or magnesium silicates with one or more alkali metal compounds. Optionally a transitional alumina can be present. The permanent binders typically impart mechanical strength to the finished carrier.

After thorough dry-mixing, sufficient water and/or other suitable liquid is added to help form the mass into a paste-like substance. Carrier particles are formed from the paste by conventional means, such as extrusion. After molding into the desired shape, the carrier particles can be calcined at a temperature from about 1000° C. to about 1600° C. to form the carrier. When the particles are formed by extrusion, it may be desirable to also include extrusion aids. The amounts of extrusion aids required depend on a number of factors that relate to the equipment used. Such factors are well within the general knowledge of a person skilled in the art of extruding ceramic materials.

In some embodiments and when alpha-alumina carriers having multimodal pore size distributions are employed, the carrier can be prepared by selecting alpha-alumina particles having a finer size than the size of the agglomerated alpha-alumina particles in the alpha-alumina powder and then added to the alpha-alumina powder to avoid pore migration. The "finer" alpha-alumina particles fill and maintain the pores that are present between adjacent agglomerated alpha-alumina particles within the alpha-alumina powder. A burnout material, as described above, can then be selected to address size, volume and percentage of pores within the final carrier. As is conventional, the final porosity of the fired carrier is substantially determined by the amount of burnout material that is added. Next, the admixture can be extruded or molded into a desired shape and then subjected to firing.

The alpha-alumina carrier that can be employed in the present invention can be in the form of particles, chunks, pellets, rings, spheres, three-holes, wagon wheels, cross-partitioned hollow cylinders, and the like, of a size preferably suitable for employment in fixed bed reactors. In one embodiment, the carrier particles typically have equivalent diameters in the range of from 3 mm to 12 mm, and more typically in the range of from 5 mm to 10 mm, which are usually compatible with the internal diameter of the tubular reactors in which the catalyst is placed. As known in the art, the term "equivalent diameter" is used to express the size of an irregularly-shaped object by expressing the size of the object in terms of the diameter of a sphere having the same volume as the irregularly-shaped object. A preferred shape of the carrier is a hollow cylinder, so called Raschig ring.

The alpha-alumina carrier that can be employed in the present invention has surface characteristics (e.g., roughness and purity) and microstructure (e.g., pore size and surface area) that assist in determining the size and distribution of silver particles of the catalyst of the present invention.

The alpha-alumina carrier that can be employed in the present invention has a pore volume from 0.30 mL/gm to 0.80 mL/gm, a surface area from 0.4 $m^2$/gm to 2.0 $m^2$/gm, and an $Al_2O_3$ content of greater than 80%. The alpha-alumina carrier has a pore size distribution with at least one mode in the pore size range of 0.01-100 micrometers, as measured by mercury intrusion porosimetry.

In one embodiment of the present invention, the alpha-alumina carrier that can be employed in the present invention has a pore volume from 0.40 mL/gm to 0.70 mL/gm, a surface area from 0.7 $m^2$/gm to 1.2 $m^2$/gm, and an $Al_2O_3$ content of greater than 80%. In such an embodiment, the alpha-alumina carrier has less than 25% pores having a pore size from 0.01 micrometers to 1.0 micrometer, greater than 50% of pores having a pore size from 1.0 micrometer to 10 micrometers, and less than 25% of pores having a pore size from 10 micrometers to 100 micrometers (based on the % of total pore volume).

In another embodiment of the present invention, the alpha-alumina carrier that can be employed in the present invention has a pore volume from 0.30 mL/gm to 0.55 mL/gm, a surface area from 0.5 $m^2$/gm to 1.0 $m^2$/gm, and an $Al_2O_3$ content of greater than 85%. In such an embodiment, the alpha-alumina carrier has less than 35% of pores having a pore size from 0.01 micrometers to 1.0 micrometer, greater than 30% of pores having a pore size from 1.0 micrometer to 10 micrometers, and less than 25% of pores having a pore size from 10 micrometers to 100 micrometers (based on the % of total pore volume).

In some embodiments of the present invention, the alpha-alumina carrier that can be employed in the present invention has an initial low alkali metal content. By "low alkali metal content" it is meant that the carrier contains from about 2000 ppm or less, typically from about 30 ppm to about 300 ppm, of alkali metal therein. Carriers containing low alkali metal content can be obtained utilizing techniques that are well known in the art. For example, and in one embodiment, substantially no alkali metal(s) is(are) used during the carrier manufacturing process. By "substantially no alkali metal" it is meant that only trace amounts of alkali metal are used during the carrier manufacture process. In another embodiment, a carrier having a low alkali metal content can be obtained by performing various washing steps to the carrier precursor materials used in forming the carrier. The washing steps can include washing in water, a base or an acid.

In other embodiments of the present invention, the carrier that can be used has an alkali metal content that is above the value mentioned above for the carrier having the low alkali metal content. In such an embodiment the carrier that can be employed in the present invention typically contains a measurable level of sodium on the surface thereof. The concentration of sodium at the surface of the carrier will vary depending on the level of sodium within the different components of the carrier as well as the details of its calcination. In one embodiment of the present invention, the carrier that can be employed in the present invention has a surface sodium content of from about 5 ppm to about 200 ppm, relative to the total mass of the carrier. In another embodiment of the present invention, the carrier that can be employed in the present invention has a surface sodium content of from about 7 ppm to about 70 ppm, relative to the total mass of the carrier. The sodium content mentioned above represents that which is found at the surface of the carrier and that which can be leached, i.e., removed, by de-ionized water.

In order to produce the catalyst of the present invention, an alpha-alumina carrier having the above characteristics is then provided with greater than about 20% by weight of silver thereon and/or therein; the useful upper silver content range is typically about 50% by weight. The amount of silver that is employed in the present invention is sufficient for the catalyst to be catalytically active in the epoxidation of ethylene to ethylene oxide. In one embodiment of the present invention, the silver content that is provided to the alpha-alumina carrier is from about 25% by weight to about 35% by weight. In another embodiment of the present invention, the silver content that is provided to the alpha-aluminum carrier is from about 20% by weight to about 45% by weight. Silver content that is substantially lower than about 20% by weight will not lead to a catalyst that exhibits the improved performance properties described herein.

The catalyst can be prepared by impregnating the carrier with silver ions, compounds, complexes, and/or salts dissolved in a suitable solvent sufficient to cause deposition of a silver precursor compound onto and/or into the carrier. In some embodiments of the present invention, and as will be described in greater detail herein below, the carrier can be simultaneously impregnated and incorporated with silver along with any additional desired promoter or promoter combination, by any of the conventional methods known in the art, e.g., by excess solution impregnation, incipient wetness impregnation, spray coating, and the like. Typically, the carrier material is placed in contact with the silver-containing solution until a sufficient amount of the solution is absorbed by the carrier. Infusion of the silver-containing solution into the carrier can be aided by application of a vacuum. A single impregnation or a series of impregnations, with or without intermediate drying, may be used, depending in part on the concentration of the silver component in the solution. Impregnation procedures are described in, for example, U.S. Pat. Nos. 4,761,394, 4,766,105, 4,908,343, 5,057,481, 5,187,140, 5,102,848, 5,011,807, 5,099,041 and 5,407,888, all of which are incorporated herein by reference. Known procedures for pre-deposition, co-deposition, and post-deposition of the various promoters can also be employed.

Silver compounds useful for catalyst deposition by impregnation include, for example, silver oxalate, silver nitrate, silver oxide, silver carbonate, a silver carboxylate, silver citrate, silver phthalate, silver lactate, silver propionate, silver butyrate and higher fatty acid salts and combinations thereof. The silver solution used to impregnate the carrier can contain any suitable solvent. The solvent can be, for example, water-based, organic-based, or a combination thereof. The solvent can have any suitable degree of polarity, including highly polar, moderately polar or non-polar, or substantially or completely non-polar. The solvent typically has sufficient solvating power to solubilize the solution components. A wide variety of complexing or solubilizing agents may be employed to solubilize silver to the desired concentration in the impregnating medium. Useful complexing or solubilizing agents include amines, ammonia, lactic acid and combinations thereof. For example, the amine can be an alkylene diamine having from 1 to 5 carbon atoms. In one embodiment, the solution comprises an aqueous solution of silver oxalate and ethylene diamine. The complexing/solubilizing agent may be present in the impregnating solution in an amount from about 0.1 to about 10 moles of ethylene diamine per mole of silver, preferably from about 0.5 to about 5 moles, and more preferably from about 1 to about 4 moles of ethylene diamine for each mole of silver.

The concentration of silver salt in the solution is typically in the range from about 0.1% by weight to the maximum permitted by the solubility of the particular silver salt in the solubilizing agent employed. More typically, the concentration of silver salt is from about 0.5% to 45% by weight of silver, and even more typically, from about 5 to 35% by weight.

In addition to silver any one or more promoting species in a promoting amount can also be incorporated into the carrier either prior to, coincidentally with, or subsequent to the deposition of the silver. As used herein, a "promoting amount" of a certain component refers to an amount of that component that works effectively to provide an improvement in one or more of the catalytic properties of a subsequently formed catalyst when compared to a catalyst not containing the component. Examples of catalytic properties include, inter alia, operability (resistance to runaway), selectivity, activity, conversion, stability and yield. It is understood by one skilled in the art that one or more of the individual catalytic properties may be enhanced by the "promoting amount" while other catalytic properties may or may not be enhanced or may even be diminished. It is further understood that different catalytic properties may be enhanced at different operating conditions. For example, a catalyst having enhanced selectivity at one set of operating conditions may be operated at a different set of conditions wherein the improvement is exhibited in the activity rather than in the selectivity.

For example, catalysts of the present invention may include a promoting amount of alkali metal or a mixture of two or more alkali metals. Suitable alkali metal promoters include, for example, lithium, sodium, potassium, cesium rubidium, or combinations thereof. Thus, and in one example, a silver-based ethylene oxide catalyst including silver and one of lithium, sodium, potassium, cesium and rubidium can be provided in the present invention. The amount of alkali metal will typically range from about 10 ppm to about 3000 ppm, more typically from about 15 ppm to about 2000 ppm, more typically from about 20 ppm to about 1500 ppm, and even more typically from about 50 ppm to about 1000 ppm by weight of the total catalyst, expressed in terms of the additional alkali metal.

The catalyst of the present invention may also include a promoting amount of a Group 2 alkaline earth metal or a mixture of two or more Group 2 alkaline earth metals. Suitable alkaline earth metal promoters include, for example, beryllium, magnesium, calcium, strontium, and barium or combinations thereof. The amounts of alkaline earth metal promoters are used in similar amounts as the alkali metal promoters described above.

The catalyst of the present invention may also include a promoting amount of a main group element or a mixture of two or more main group elements. Suitable main group elements include any of the elements in Groups 13 (boron group) to 17 (halogen group) of the Periodic Table of the Elements. In one example, a promoting amount of one or more sulfur compounds, one or more phosphorus compounds, one or more boron compounds or combinations thereof can be used.

The catalyst of the present invention may also include a promoting amount of a transition metal or a mixture of two or more transition metals. Suitable transition metals can include, for example, the elements from Groups 3 (scandium group), 4 (titanium group), 5 (vanadium group), 6 (chromium group), 7 (manganese group), 8-10 (iron, cobalt, nickel groups), and 11 (copper group) of the Periodic Table of the Elements, as well as combinations thereof. More typically, the transition metal is an early transition metal selected from Groups 3, 4, 5, 6, or 7 of the Periodic Table of Elements, such as, for example, hafnium, yttrium, molybdenum, tungsten, rhenium, chromium, titanium, zirconium, vanadium, tantalum, niobium, or a combination thereof.

In one embodiment of the present invention, the catalyst of the present invention includes silver, cesium, and rhenium. In another embodiment of the present invention, the catalyst of the present invention includes silver, cesium, rhenium and one or more species selected from Li, K, W, Zn, Mo, Mn, and S.

The catalyst of the present invention may also include a promoting amount of a rare earth metal or a mixture of two or more rare earth metals. The rare earth metals include any of the elements having an atomic number of 57-71, yttrium (Y) and scandium (Sc). Some examples of these elements include lanthanum (La), cerium (Ce), and samarium (Sm).

The transition metal or rare earth metal promoters are typically present in an amount of from about 0.1 micromoles per gram to about 10 micromoles per gram, more typically from about 0.2 micromoles per gram to about 5 micromoles per gram, and even more typically from about 0.5 micromoles per gram to about 4 micromoles per gram of total catalyst, expressed in terms of the metal.

All of these promoters, aside from the alkali metals, can be in any suitable form, including, for example, as zerovalent metals or higher valent metal ions.

After impregnation with silver, and any promoters, the impregnated carrier is removed from the solution and calcined for a time sufficient to reduce the silver component to metallic silver and to remove volatile decomposition products from the silver-containing carrier. The calcination is typically accomplished by heating the impregnated carrier, preferably at a gradual rate, to a temperature in a range of about 200° C. to about 600° C., more typically from about 200° C. to about 500° C., more typically from about 250° C. to about 500° C., and more typically from about 200° C. or 300° C. to about 450° C., at a reaction pressure in a range from about 0.5 to about 35 bar. In general, the higher the temperature, the shorter the required calcination period. A wide range of heating periods have been described in the art for the thermal treatment of impregnated carriers. See, for example, U.S. Pat. No. 3,563,914, which indicates heating for less than 300 seconds, and U.S. Pat. No. 3,702,259, which discloses heating from 2 to 8 hours at a temperature of from 100° C. to 375° C. to reduce the silver salt in the catalyst. A continuous or step-wise heating program may be used for this purpose. During calcination, the impregnated carrier is typically exposed to a gas atmosphere comprising oxygen, such as air, or an inert gas, such as nitrogen, or both. The inert gas may also include a reducing agent.

In some embodiments of the present invention, multiple silver impregnation steps are performed. By "multiple-impregnation" it is meant, that the present invention contemplates at least two separate silver loading steps and at least two separate calcination steps as will be described in greater detail herein below. In such an embodiment, a first amount of silver is deposited on and/or in the carrier to provide a first catalyst precursor composition including a first amount of silver disposed on and/or in the carrier. By "first catalyst precursor composition" it is meant a composition that includes a carrier having non-activated silver ions disposed on and/or in the carrier and, as such, the first catalyst precursor composition is not capable of epoxidating ethylene to ethylene oxide in the presence of molecular oxygen.

The first catalyst precursor composition can be prepared by introducing a first silver-containing solution to the alpha-alumina carrier described above. The first silver-containing solution that is employed in the present invention contains silver and optionally, part of the promoters (some of them or all of them). In a preferred embodiment of the present invention, the first silver-containing solution does not contain any promoter therein. More particularly, the first silver-containing solution contains silver ions, compounds, complexes, and/or salts that are dissolved in a solvent. The first-silver-containing solution may include one of the silver-containing solutions mentioned above. The first amount, i.e., concentration, of silver in the first silver-containing solution is typically in the range from about 0.1% by weight to the maximum permitted by the solubility of the particular silver compound in the solubilizing agent employed. More typically, the first amount, i.e., concentration, of silver in the first silver-containing solution is from about 0.5% to about 45% by weight of silver, and even more typically, from about 5 to about 35% by weight.

Next, the first catalyst precursor composition is removed from the solution and thereafter subjected to a first calcination to provide a first silver-containing catalyst composition having a first silver content with some promoters or without promoters disposed on and/or in the alpha-alumina carrier. The first calcination is performed for a time sufficient to reduce the silver component to metallic silver and to remove volatile decomposition products from the first silver-containing catalyst composition. The first calcination is typically accomplished by heating the first catalyst precursor composition including the first amount of silver, preferably at a gradual rate, to a temperature in a range of about 200° C. to about 600° C., more typically from about 200° C. to about 500° C., more typically from about 250° C. to about 500° C., and more typically from about 200° C. or 300° C. to about 450° C., at a reaction pressure in a range from about 0.5 to about 35 bar. During the first calcination, the first silver-containing catalyst composition including the first amount of silver with some promoters or without promoters can be exposed to a gas atmosphere comprising oxygen, such as air, or an inert gas, such as nitrogen, or both. The inert gas may also include a reducing agent.

After subjecting the first silver-containing catalyst composition to the first calcination, the first silver-containing catalyst composition having the first silver content with or without promoters is provided on the carrier. In one embodiment of the present invention, the first silver content of the first silver-containing catalyst composition disposed on and/or in the carrier is from about 3 weight % to about 30 weight %, based on the total weight of the carrier. In another embodiment of the present invention, the silver content of the first silver-containing catalyst composition disposed on and/or in the carrier is from about 10 weight % to about 25 weight %, based on the total weight of the carrier.

Next, a second amount of silver and a promoting amount of one or more promoters are introduced coincidentally during a second deposition to the carrier containing the first silver-containing catalyst composition. The second deposition provides a second catalyst precursor composition having a second silver content that is greater than the first silver content and a promoting amount of one or more promoters disposed on and/in the carrier. By "second catalyst precursor composition" it is meant a second composition that includes a carrier having non-activated silver ions and promoter ions disposed on and/or in the carrier and, as such, the second catalyst precursor composition is not capable of epoxidating ethylene to ethylene oxide in the presence of molecular oxygen.

The second catalyst precursor composition can be prepared by introducing a second silver-containing solution to the carrier that contains the first silver-containing catalyst composition. The second silver-containing solution is similar to the first silver-containing solution except that it contains one or more promoters in a promoting amount (or in an amount smaller than the promoting amount by the promoters' content used in the first impregnation) also dissolved in the solution. The second amount, i.e., concentration, of silver in the second silver-containing solution is typically in the range from about 0.1% by weight to the maximum permitted by the solubility of the particular silver compound in the solubilizing agent employed. More typically, the second amount, i.e., concentration, of silver is from about 0.5% to about 45% by weight of silver, and even more typically, from about 5 to about 35% by weight.

As mentioned above, the second silver-containing solution also includes a promoting amount of one or more promoters therein. The types of promoters and the "promoting amount" that can be used in this embodiment of the present invention are the same as those previously discussed above. In one embodiment of the present invention, the second silver-containing solution includes silver, cesium, and rhenium. In another embodiment of the present invention, the second silver-containing solution includes silver, cesium, rhenium, and one or more species selected from Li, K, W, Zn, Mo, Mn, and S. In a further embodiment of the present invention, the second silver-containing solution includes silver, cesium, rhenium and one or more species selected from Li and S.

Next, the second catalyst precursor composition is removed from the second silver-containing solution and thereafter subjected to a second calcination to provide a second silver-containing catalyst composition having a second silver content that is greater than the first silver content on the carrier. The second calcination is performed for a time sufficient to reduce silver components to metallic silver and to remove volatile decomposition products from the second silver-containing catalyst composition. The second calcination is typically accomplished by heating the second catalyst precursor composition including the second amount of silver within calcination conditions mentioned in the previously embodiment of the present invention. During the second calcination, the second catalyst precursor composition can be exposed to a gas atmosphere comprising oxygen, such as air, or an inert gas, such as nitrogen or both. The inert gas may also include a reducing agent.

In some embodiments of the present invention, further silver impregnations with or without promoters can be performed following the second calcination step. In such embodiments, a calcination step may follow each impregnation step. Alternative, and after the initial first calcination, a single calcination may follow multiple impregnation steps.

The catalyst (prior to use) of the present invention has silver particles having a diameter of greater than about 150 nm and a distribution density of about 20 particles per 1 square micron or less; the lower value for the distribution density is typically about 1 particle per 1 square micron, while the upper value for the silver particle diameter is typically about 300 nm. In some embodiments of the present invention, the silver particles have a diameter from about 150 nm to about 300 nm. In yet other embodiments, the silver particles have a diameter from about 170 nm to about 250 nm. In some embodiments of the present invention, the catalyst has a silver particle density of from about 5 particles per 1 square micron to about 20 particles per 1 square micron. In yet other embodiments of the present invention, the catalyst has a silver particle density of from about 10 particles per 1 square micron to about 20 particles per 1 square micron.

The catalyst of the present invention, which has high silver content (about 20% by weight or greater), a silver particle size diameter of greater than about 150 nm, and a silver particle distribution density of about 20 particles per 1 square micron or less, has improved useful lifetime as evident by having a reduced selectivity decline rate and/or a reduced activity decline rate as compared to a catalyst that does not include the high amount of silver, the silver particle size and silver particle distribution density.

In another aspect, the present invention is directed to a method for the vapor phase production of ethylene oxide by conversion of ethylene to ethylene oxide in the presence of oxygen by use of the catalyst described above. In some embodiments of the present invention, and prior to ethylene oxide production, the catalyst of the present invention can undergo a catalyst start-up process. The catalyst start-up process conditions the catalyst and facilitates the readiness of the catalyst for ethylene oxide production. The type of start-up process that can be used in the present invention is not limited to any specific type.

Generally, the ethylene oxide production process is conducted by continuously contacting an oxygen-containing gas with ethylene in the presence of the catalyst at a temperature in the range from about 180° C. to about 330° C., more typically from about 200° C. to about 325° C., and more typically from about 225° C. to about 270° C., at a pressure which may vary from about atmospheric pressure to about 30 atmospheres depending on the mass velocity and productivity desired. A typical process for the oxidation of ethylene to ethylene oxide comprises the vapor phase oxidation of ethylene with molecular oxygen in the presence of the catalyst of the present invention in a fixed bed, tubular reactor. Conventional commercial fixed bed ethylene oxide reactors are typically in the form of a plurality of parallel elongated tubes (in a suitable shell). In one embodiment, the tubes are approximately 0.7 to 2.7 inches O.D. and 0.5 to 2.5 inches I.D. and 15-45 feet long filled with catalyst.

The catalyst of the present invention has been shown to be particularly selective catalysts in the oxidation of ethylene with molecular oxygen to ethylene oxide. Selectivity values of at least about 83 mol % up to about 93 mol % are typically achieved. In some embodiments, the selectivity is from about 87 mol % to about 93 mole %. The conditions for carrying out such an oxidation reaction in the presence of the catalyst of the present invention broadly comprise those described in the prior art. This applies, for example, to suitable temperatures, pressures, residence times, diluent materials (e.g., nitrogen, carbon dioxide, steam, argon, and methane), the presence or absence of moderating agents to control the catalytic action (e.g., 1,2-dichloroethane, vinyl chloride or ethyl chloride), the desirability of employing recycle operations or applying successive conversion in different reactors to increase the yields of ethylene oxide, and any other special conditions which may be selected in processes for preparing ethylene oxide.

In the production of ethylene oxide, reactant feed mixtures typically contain from about 0.5 to about 45% ethylene and from about 3 to about 15% oxygen, with the balance comprising comparatively inert materials including such substances as nitrogen, carbon dioxide, methane, ethane, argon and the like. Only a portion of the ethylene is typically reacted per pass over the catalyst. After separation of the desired ethylene oxide product and removal of an appropriate purge stream and carbon dioxide to prevent uncontrolled build up of inert products and/or byproducts, unreacted materials are typically returned to the oxidation reactor. For purposes of illustration only, the following are conditions that are often used in current commercial ethylene oxide reactor units: a gas hourly space velocity (GHSV) of 1500-10,000 $h^{-1}$, a reactor inlet pressure of 150-400 psig, a coolant temperature of 180-315° C., an oxygen conversion level of 10-60%, and an EO production (work rate) of 100-500 kg EO per cubic meters of catalyst per hour. More typically, the feed composition at the reactor inlet comprises 1-40% ethylene, 3-12% oxygen, 0.3-40% $CO_2$, 0-3% ethane, 0.3-20 ppmv total concentration of organic chloride moderator, and the balance of the feed comprised of argon, methane, nitrogen, or mixtures thereof.

The resulting ethylene oxide is separated and recovered from the reaction products using methods known in the art. The ethylene oxide process may include a gas recycle process wherein a portion or substantially all of the reactor effluent is readmitted to the reactor inlet after substantially removing the ethylene oxide product and byproducts. In the recycle mode, carbon dioxide concentrations in the gas inlet to the reactor may be, for example, from about 0.3 to about 6, preferably from about 0.3 to about 2.0, volume percent.

Examples have been set forth below for the purpose of further illustrating the present invention. The scope of the present invention is not to be in any way limited by the examples set forth herein.

In the following examples, Carrier 1 denotes an alpha-alumina carrier that has a pore volume within the range from 0.40 mL/gm to 0.55 mL/gm, a surface area within the range from 0.7 $m^2$/gm to 1.2 $m^2$/gm, an $Al_2O_3$ content of greater than 80% and has pore sizes from 0.01 micrometers to 1.0 micrometer of less than 25%, pore sizes from 1.0 micrometer to 10 micrometers of greater than 50%, and pore sizes from 10 micrometers to 100 micrometers of less than 25% (based on the % of total pore volume). The carrier was washed prior to introducing silver and the other promoters to the carrier.

Carrier 2 denotes an alpha-alumina carrier that has a pore volume within the range from 0.35 mL/gm to 0.42 mL/gm, a surface area within the range from 0.5 $m^2$/gm to 1.0 $m^2$/gm, an $Al_2O_3$ content of greater than 85% and has pore sizes from 0.01 micrometer to 1.0 micrometer of less than 35%, pore sizes from 1.0 micrometer to 10 micrometers of greater than 30%, and pore sizes from 10 micrometers to 100 micrometers of less than 25% (based on the % of total pore volume). The carrier was washed prior to introducing silver and the other promoters to the carrier.

Silver Stock Solution for silver-based ethylene oxide catalyst: A silver solution containing roughly 30 wt % silver, and having a specific gravity of 1.55 g/mL was prepared by first adding a quantity of ethylenediamine to deionized water. Oxalic acid dihydrate was then added to the water-ethylenediamine solution in small portions. After all oxalic acid was dissolved, high purity silver oxide was added to solution in small portions. After all silver oxide was dissolved and the solution was cooled to about 35° C. it was removed from the cooling bath.

Inventive Catalyst Preparation: A 150 g portion of the one of the mentioned carriers was placed in a flask and evacuated to about 0.1 torr prior to impregnation. The silver solution was aspirated into the evacuated flask to cover the carrier while maintaining the pressure at about 0.1 torr. The vacuum was released after about 5 minutes to restore ambient pressure, hastening complete penetration of the solution into the pores. Subsequently, the excess impregnation solution was drained from the impregnated carrier. Calcination of the wet silver-containing precursor catalyst was done on a moving belt calciner. In this unit, the wet silver-containing catalyst precursor was transported on a stainless steel belt through a multi-zone furnace. All zones of the furnace were continuously purged with pre-heated, ultra-high purity nitrogen and the temperature was increased gradually as the precursor catalyst passes from one zone to the next. The heat was radiated from the furnace walls and from the preheated nitrogen. The wet precursor catalyst entered the furnace at ambient temperature. The temperature in the precursor catalyst layer was then increased gradually to a maximum of about 400° C. as the catalyst passed through the heated zones. In the last (cooling) zone, the temperature of the now formed first silver-containing catalyst composition was immediately lowered to less than 100° C. before it emerged into ambient atmosphere. The total residence time in the furnace was approximately 45 minutes.

Following the calcination, the first silver-containing catalyst composition was placed in a flask and evacuated to about 0.1 torr prior to impregnation. To the above silver stock solution were added aqueous solutions of promoters including rhenium as ammonium per-rhenate and cesium as cesium hydroxide, in sufficient concentrations to prepare a second catalyst composition having a promoting amount of promoters. After thorough mixing, the promoted silver solution was aspirated into the evacuated flask to cover the carrier while maintaining the pressure at about 0.1 torr. The vacuum was released after about 5 minutes to restore ambient pressure, hastening complete penetration of the solution into the pores. Subsequently, the excess impregnation solution was drained from the impregnated carrier. Calcination of the wet silver-promoter catalyst precursor was done on a moving belt calciner, as described above.

Reference Catalyst Preparation: A 150 g portion of the above mentioned carrier was placed in a flask and evacuated to about 0.1 torr prior to impregnation. To the above silver stock solution were added aqueous solutions of promoters including cesium as cesium hydroxide and rhenium as ammonium per-rhenate, in sufficient concentrations to prepare a catalyst composition; the type of promoters and amounts used for the reference catalyst preparation are the same as the inventive catalyst preparation. After thorough mixing, the promoted silver solution was aspirated into the evacuated flask to cover the carrier while maintaining the pressure at about 0.1 torr. The vacuum was released after about 5 minutes to restore ambient pressure, hastening complete penetration of the solution into the pores. Subsequently, the excess impregnation solution was drained from the impregnated carrier.

Calcination of the wet catalyst was done on a moving belt calciner. In this unit, the wet catalyst was transported on a stainless steel belt through a multi-zone furnace. All zones of the furnace were continuously purged with pre-heated, ultra-high purity nitrogen and the temperature was increased gradually as the catalyst passes from one zone to the next. The heat was radiated from the furnace walls and from the preheated nitrogen. The wet catalyst entered the furnace at ambient temperature. The temperature in the catalyst layer was then increased gradually to a maximum of about 400° C. as the catalyst passed through the heated zones. In the last (cooling) zone, the temperature of the now activated silver-based ethylene oxide catalyst was immediately lowered to less than 100° C. before it emerged into ambient atmosphere. The total residence time in the furnace was approximately 45 minutes.

Example 1

Reference catalyst 1 containing 16% by weight silver and a promoting amount of at least cesium (Cs) and rhenium (Re) was prepared on Carrier 1 as described above. Reference catalyst 1, prior to use (i.e., a fresh sample), had an average Ag particle size of 121 nm and an Ag particle distribution density of 23 Ag particles per 1 $\mu m^2$.

Reference catalyst 1 was used for about 1 month in a laboratory micro-reactor at $\Delta EO=2.2$ mol %, and the following feed composition: $[C_2H_4]=15\%$, $[O_2]=7\%$, $[CO_2]=2\%$, and $N_2$ balance gas. After use, reference catalyst 1 had an average Ag particle size of 320 nm and an Ag particle distribution density of 1.40 Ag particles per 1 $\mu m^2$.

Reference catalyst 1 exhibited selectivity decline rate $\Delta S/\Delta t=5.1$ selectivity points per month and activity decline rate $\Delta T/\Delta t=11.2°$ C./month under the laboratory micro-reactors testing conditions.

Example 2

Inventive catalyst 1 containing 27% by weight silver and the same promoters and promoter amounts as Example 1 was prepared on Carrier 1 as described above. Inventive catalyst 1, prior to use (i.e., a fresh sample), had an average Ag particle size of 174 nm (~44% increase in particle size over fresh reference catalyst in Example 1) and an Ag particle distribution density of 20 Ag particles per 1 $\mu m^2$ (~13% decrease as compared to fresh reference catalyst 1 of Example 1).

Inventive catalyst 1 was used for about 1 month in a laboratory micro-reactor at $\Delta EO=2.2$ mol %, and the following feed composition: $[C_2H_4]=15\%$, $[O_2]=7\%$, $[CO_2]=2\%$, and $N_2$ balance gas. After use, inventive catalyst 1 had an average Ag particle size of 292 nm (~9% decrease in particle size as compared to spent reference catalyst 1) and an Ag particle distribution density of 1.95 Ag particles per 1 $\mu m^2$ (39% increase in particle distribution density over spent reference catalyst 1 of Example 1).

Inventive catalyst 1 exhibited selectivity decline rate $\Delta S/\Delta t=1.8$ selectivity points per month and activity decline rate $\Delta T/\Delta t=6.1°$ C./month under the laboratory micro-reactors testing conditions. This is a substantial improvement of catalyst stability (both selectivity and activity) over reference catalyst 1 on the same Carrier 1 reported in Example 1. The stability improvement is due to specific combination of Ag particle size and their distribution density on the carrier.

Example 3

Reference catalyst 2 containing 16% by weight silver and a promoting amount of at least cesium (Cs) and rhenium (Re) was prepared on Carrier 2 as described above. Reference catalyst 2, prior to use (i.e., a fresh sample), had an average Ag particle size of 149 nm and an Ag particle distribution density of 19.7 Ag particles per 1 $\mu m^2$.

Reference catalyst 2 was used for about 1 month in a laboratory micro-reactor at $\Delta EO=2.2$ mol %, and the following feed composition: $[C_2H_4]=15\%$, $[O_2]=7\%$, $[CO_2]=2\%$, and $N_2$ balance gas. After use, reference catalyst 2 had an average Ag particle size of 338 nm and an Ag particle distribution density of 1.55 Ag particles per 1 $\mu m^2$.

The reference catalyst 2 of Example 3 exhibited selectivity decline rate $\Delta S/\Delta t=5.6$ selectivity points per month and activity decline rate $\Delta T/\Delta t=17.4°$ C./month under the laboratory micro-reactors testing conditions.

Example 4

Inventive catalyst 2 containing 25% by weight silver and the same promoters and promoter amounts as Example 2 was prepared on Carrier 2 as described above. Inventive catalyst 2, prior to use (i.e., a fresh sample) had an average Ag particle size of 173 nm (~16% increase in particle size over fresh reference catalyst 2 of Example 3) and an Ag particle distribution density of 17.5 Ag particles per 1 $\mu m^2$ (~11% decrease as compared to fresh reference catalyst 2 in Example 3).

Inventive catalyst 2 was used for about 1 month in a laboratory micro-reactor at $\Delta EO=2.2$ mol %, and the following feed composition: $[C_2H_4]=15\%$, $[O_2]=7\%$, $[CO_2]=2\%$, and $N_2$ balance gas. After use, inventive catalyst 2 had an average Ag particle size of 365 nm (~8% increase in particle size over the spent reference catalyst 2 in Example 3) and an Ag particle distribution density of 1.36 Ag particles per 1 $\mu m^2$ (12% decrease in particle distribution density as compared to spent reference catalyst 2 in Example 3).

The inventive catalyst 2 of Example 4 exhibited selectivity decline rate $\Delta S/\Delta t=1.8$ selectivity points per month and activity decline rate $\Delta T/\Delta t=11.0°$ C./month under the laboratory micro-reactors testing conditions. This is a substantial improvement of catalyst stability (both selectivity and activity) over reference catalyst 2 on the same Carrier 2 reported in Example 3. The stability improvement is due to specific combination of Ag particle size and their distribution density on the carrier.

Table 1 summaries the reference and inventive catalysts of Examples 1-4, and provides a tabular form of the data described above.

TABLE I

| Catalyst | Properties of Fresh Catalysts Distribution | | Properties of Spent Catalysts Distribution | | Catalyst Performance | |
|---|---|---|---|---|---|---|
| | Average Ag Particle Size (nm) | Density of Ag Particles (1/μm²) | Average Ag Particle Size (nm) | Density of Ag Particles (1/μm²) | ΔS/Δt (sel. points/ month) | ΔT/Δt (° C./ month) |
| Example 1 Reference catalyst 1 on Carrier 1 ([Ag] = 16 wt %) | 121 | 23.0 | 320 | 1.40 | 5.1 | 11.2 |
| Example 2 Inventive catalyst 1, on Carrier 1 ([Ag] = 27 wt %) | 174 | 20.0 | 292 | 1.95 | 1.8 | 6.1 |
| Example 3 Reference catalyst 2 on Carrier 2 ([Ag] = 16 wt %) | 149 | 19.7 | 338 | 1.55 | 5.6 | 17.4 |
| Example 4 Inventive catalyst 2 on Carrier 2 ([Ag] = 25 wt %) | 173 | 17.5 | 365 | 1.36 | 1.8 | 11.0 |

While the present invention has been particularly shown and described with respect to various embodiments thereof, it will be understood by those skilled in the art that the foregoing and other changes in forms and details may be made without departing from the spirit and scope of the present invention. It is therefore intended that the present invention not be limited to the exact forms and details described and illustrated, but fall within the scope of the appended claims.

What is claimed is:

1. A silver-based ethylene epoxidation catalyst comprising:
   greater than about 20% by weight of silver disposed on an alpha-alumina carrier; and
   a promoting amount of one or more promoters disposed on said alpha-alumina carrier, wherein said silver is present on said alpha-alumina carrier as silver particles, said silver particles having a diameter of greater than about 150 nm and having a distribution density of about 20 particles per 1 square micron or less.

2. The silver-based ethylene epoxidation catalyst of claim 1, wherein said one or more promoters comprise Group IIA metal promoters, one or more transition metals, one or more alkali metals or any combination thereof.

3. The silver-based ethylene epoxidation catalyst of claim 2, wherein said one or more transition metals are selected from the group consisting of Groups 4-10 of the Periodic Table of the Elements.

4. The silver-based ethylene epoxidation catalyst of claim 3, wherein said one or more transition metals are selected from the group consisting of molybdenum, rhenium, tungsten, chromium, titanium, hafnium, zirconium, vanadium, thorium, tantalum, and niobium.

5. The silver-based ethylene epoxidation catalyst of claim 2, wherein said one or more transition metals comprise rhenium, molybdenum, tungsten, or any combination thereof.

6. The silver-based ethylene epoxidation catalyst of claim 2, wherein said one or more alkali metals are selected from the group consisting of cesium, lithium, sodium, potassium, and rubidium.

7. The silver-based ethylene epoxidation catalyst of claim 6, wherein said one or more alkali metals comprise lithium and cesium.

8. The silver-based ethylene epoxidation catalyst of claim 1, wherein said diameter of said silver particles is from about 150 nm to about 300 nm.

9. The silver-based ethylene epoxidation catalyst of claim 1, wherein said distribution density of said silver particles is from about 10 particles per 1 square micron to about 20 particles per 1 square micron.

10. The silver-based ethylene epoxidation catalyst of claim 1, wherein said alpha-alumina carrier has a pore volume from 0.40 mL/gm to 0.70 mL/gm, a surface area from 0.7 m²/gm to 1.2 m²/gm, an Al₂O₃ content of greater than 80% and has a pore size from 0.01 micrometers to 1.0 micrometer of less than 25%, pore size from 1.0 micrometer to 10 micrometers of greater than 50%, and pore size from 10 micrometers to 100 micrometers of less than 25%.

11. The silver-based ethylene epoxidation catalyst of claim 1, wherein said alpha-alumina carrier has a pore volume from 0.33 mL/gm to 0.55 mL/gm, a surface area from 0.5 m²/gm to 1.0 m²/gm, an Al₂O₃ content of greater than 85% and has a pore size from 0.01 micrometers to 1.0 micrometer of less than 35%, pore size from 1.0 micrometer to 10 micrometers of greater than 30%, and pore size from 10 micrometers to 100 micrometers of less than 25%.

12. The silver-based ethylene epoxidation catalyst of claim 1, wherein said one or more promoters comprise a promoting combination of rhenium, cesium and lithium.

13. The silver-based ethylene epoxidation catalyst of claim 1, wherein from about 20 to about 45% by weight of silver is disposed on said alpha-alumina carrier.

14. A process for the vapor phase conversion of ethylene to ethylene oxide in the presence of oxygen, said process comprising:
   providing a silver-based ethylene epoxidation catalyst to an ethylene oxide reactor, wherein said silver-based ethylene epoxidation catalyst comprises:
      greater than about 20% by weight of silver disposed on an alpha-alumina carrier; and
      a promoting amount of one or more promoters disposed on said alpha-alumina carrier, wherein said silver is present on said alpha-alumina carrier as silver particles, said silver particles having a diameter of greater than about 150 nm and having a distribution density of about 20 particles per 1 square micron or less; and reacting a reaction mixture comprising ethylene and oxygen in the present of said ethylene epoxidation catalyst.

15. A silver-based ethylene epoxidation catalyst comprising:

from about 20% to about 50% by weight of silver disposed on an alpha-alumina carrier; and a promoting amount of one or more promoters disposed on said alpha-alumina carrier, wherein said silver is present on said alpha-alumina carrier as silver particles, said silver particles having a diameter of greater than about 150 nm and up to about 300 nm, and having a distribution density of from about 1 particle per 1 square micron to about 20 particles per 1 square micron.

* * * * *